(12) United States Patent
Sunwoo et al.

(10) Patent No.: US 11,051,716 B2
(45) Date of Patent: *Jul. 6, 2021

(54) METHOD AND APPARATUS FOR JAUNDICE DIAGNOSIS BASED ON AN IMAGE

(71) Applicant: AJOU UNIVERSITY INDUSTRY-ACADEMIC COOPERATION FOUNDATION, Suwon-si (KR)

(72) Inventors: Myung Hoon Sunwoo, Seoul (KR); Jung Won Lee, Seoul (KR); Jin Hong Kim, Yongin-si (KR)

(73) Assignee: AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 412 days.

This patent is subject to a terminal disclaimer.

(21) Appl. No.: 16/115,821

(22) Filed: Aug. 29, 2018

(65) Prior Publication Data

US 2019/0110716 A1 Apr. 18, 2019

(30) Foreign Application Priority Data

Oct. 13, 2017 (KR) .................. 10-2017-0133524

(51) Int. Cl.
*A61B 5/00* (2006.01)
*A61B 5/103* (2006.01)
(Continued)

(52) U.S. Cl.
CPC .............. *A61B 5/1034* (2013.01); *A61B 3/10* (2013.01); *A61B 5/0077* (2013.01);
(Continued)

(58) Field of Classification Search
CPC ....... A61B 5/1034; A61B 3/10; A61B 5/0077; A61B 5/1032; A61B 5/441; A61B 5/6803;
(Continued)

(56) References Cited

U.S. PATENT DOCUMENTS

2010/0245541 A1* 9/2010 Zhao .................. G01D 1/00
 348/45
2014/0268037 A1* 9/2014 Siminou .............. A61B 3/0083
 351/205

(Continued)

FOREIGN PATENT DOCUMENTS

JP 2015-9140 A 1/2015
JP 2016-516475 A 6/2016

OTHER PUBLICATIONS

Communication dated Jan. 28, 2019, issued by the Korean Patent Office in counterpart Korean Patent Application No. 10-2017-0133524.

*Primary Examiner* — Keith M Raymond
*Assistant Examiner* — Adam D. Kolkin
(74) *Attorney, Agent, or Firm* — Sughrue Mion, PLLC

(57) ABSTRACT

Disclosed are a method and an apparatus for jaundice diagnosis based on an image. The method for jaundice diagnosis based on an image includes: receiving a jaundice diagnostic image acquired by photographing both a specific body part of a user and a reference object at a place where the user is positioned at present; generating color distortion information indicating a color distortion degree of the reference object included in the jaundice diagnostic image; generating a jaundice diagnostic correction image by correcting color distortion of the jaundice diagnostic image based on the color distortion information; and diagnosing a jaundice symptom for the user by using the jaundice diagnostic correction image.

5 Claims, 8 Drawing Sheets

(a)

(b)

(51) Int. Cl.
*G06T 7/90* (2017.01)
*G06T 7/00* (2017.01)
*A61B 3/10* (2006.01)

(52) U.S. Cl.
CPC ............ *A61B 5/1032* (2013.01); *A61B 5/441* (2013.01); *A61B 5/6803* (2013.01); *A61B 5/6898* (2013.01); *G06T 7/0014* (2013.01); *G06T 7/90* (2017.01); *A61B 2576/00* (2013.01); *G06T 2207/10024* (2013.01); *G06T 2207/20172* (2013.01); *G06T 2207/30041* (2013.01); *G06T 2207/30088* (2013.01)

(58) Field of Classification Search
CPC ..... A61B 5/6898; A61B 2576/00; G06T 7/90; G06T 7/0014; G06T 2207/10024; G06T 2207/20172; G06T 2207/30041; G06T 2207/30088
See application file for complete search history.

(56) References Cited

U.S. PATENT DOCUMENTS

2015/0359459 A1* 12/2015 Taylor .................. A61B 3/0083
                                                         351/205
2019/0110716 A1* 4/2019 Sunwoo ............... A61B 5/6898

* cited by examiner

METHOD AND APPARATUS FOR JAUNDICE DIAGNOSIS BASED ON AN IMAGE

CROSS-REFERENCE TO RELATED APPLICATIONS

This application claims the priority of Korean Patent Application No. 10-2017-0133524 filed on Oct. 13, 2017, in the Korean Intellectual Property Office, the disclosure of which is incorporated herein by reference.

BACKGROUND

Field

The present disclosure relates to jaundice diagnosis, and more particularly, to a method and an apparatus for jaundice diagnosis based on an image.

Description of the Related Art

Jaundice means that yellow bilirubin, which is produced during decomposition of a special protein containing iron, such as hemoglobin in the body is excessively accumulated more than needed in the body and colored yellow on the whites of the eyes (sclera), skin, mucous membranes, and the like.

There are some problems with conventional diagnostic methods for diagnosing jaundice based on a scientific view or serological test. There is a problem of subjective and objective diagnosis when jaundice is diagnosed through a visual examination, which is a physical examination that diagnoses jaundice with the naked eye. Therefore, in order to confirm jaundice, patient's blood should be sampled and blood bilirubin should be measured. Only when jaundice suspects visit a medical institution equipped with a device capable of measuring the blood bilirubin, it is possible to confirm the jaundice and a time is delayed until an examination result value is obtained after blood collection.

In addition, patients with jaundice should periodically visit a hospital to check for signs of illness during a treatment period and there is a problem that accessibility to healthcare services deteriorates when a patient lives far away from a medical institution or a patient's condition is not able to visit the medical institution periodically.

In addition, when acquiring lesion image data with an external device such as a smart phone, color of a lesion site may be distorted due to various external environments such as illumination, and image data of an accurate focus may not be acquired due to an external factor such as a hand shake of a photographer.

In this regard, Korean Patent Publication No. 10-2014-0108649, entitled "Video games to monitor retinal disease" is present.

SUMMARY

An object of the present disclosure is to provide a method and an apparatus for jaundice diagnosis based on an image, which are used for diagnosing jaundice of a user remotely.

Another object of the present disclosure is to provide a method and an apparatus for jaundice diagnosis based on an image, which are capable of preventing external factors such as hand tremor that may occur during image acquisition and correcting color distortion of a lesion site due to various illumination environments.

The technical objects of the present disclosure are not restricted to the aforementioned technical objects, and other objects of the present disclosure, which are not mentioned above, will become more apparent to one of ordinary skill in the art to which the present disclosure pertains by referencing the detailed description of the present disclosure given below.

According to an aspect of the present disclosure, there is provided a method for diagnosing jaundice based on an image by a jaundice diagnosing apparatus, including: receiving a jaundice diagnostic image acquired by photographing both a specific body part of a user and a reference object; generating color distortion information indicating a color distortion degree of the reference object included in the jaundice diagnostic image; generating a jaundice diagnostic correction image by correcting color distortion of the jaundice diagnostic image based on the color distortion information; and diagnosing a jaundice symptom for the user by using the jaundice diagnostic correction image, in which the reference object is an attachment type patch.

Preferably, the attachment type patch may be constituted by a plurality of regions having a white color and at least one different color.

Preferably, in the attachment type patch, a pattern may be formed, in which a first region and a second region of the same color are cross-disposed with a white region interposed therebetween.

Preferably, the attachment type patch may be attached to a face within a certain distance from the eye of the user or attached to a tool or the face within a certain distance from the eye when the tool is used to widen the scope of the eye sclera.

Preferably, the method may further include, before the receiving of the jaundice diagnostic image, automatically photographing an image at a point of time when the reference object is detected by analyzing an image displayed through a photographing unit provided in the jaundice diagnosing apparatus in real time, in which the photographed image may be a jaundice diagnostic image.

Preferably, when a reference image acquired by photographing the reference object under a pre-stored reference light source is a YCbCr format and the jaundice diagnostic image is an RGB format, the generating of the color distortion information includes converting the jaundice diagnostic image into the YCbCr format to generate a jaundice diagnostic conversion image and calculating a first luminance distribution function which is a cumulative probability density function for luminance values Y of all pixels belonging to the jaundice diagnostic conversion image and generating the calculated first luminance distribution function as the color distortion information and in the generating of the jaundice diagnostic correction image, the jaundice diagnostic correction image may be generated by correcting the jaundice diagnostic conversion image corresponding to the first luminance distribution function to have a second luminance distribution function which is a cumulative probability density function for the luminance values Y for all pixels belonging to the reference image.

According to an exemplary embodiment of the present disclosure, it is possible to remotely diagnose jaundice of a user, thereby reducing time and economic waste caused when the user without jaundice symptoms visits a hospital and a doctor need not unnecessarily treat the user without jaundice, which can reduce working hours of the doctor.

Further, according to another exemplary embodiment of the present disclosure, a diagnosis result of a jaundice symptom automatically calculated on the basis of an image for diagnosis of jaundice, medical history information of the user, medical information on the other person having the jaundice symptom, and the like is provided as auxiliary data to achieve diagnosis and prescription of the jaundice, thereby reducing a medical burden of the doctor.

According to yet another exemplary embodiment of the present disclosure, the user can be diagnosed with the jaundice symptom at any time, thereby enabling early diagnosis of disease.

According to still yet another exemplary embodiment of the present disclosure, a patch used as an assistant tool of image photographing is used as an auxiliary means of automatic focus recognition and at the same time, corrects color distortion of a lesioned region photographed in various illumination environments, thereby enhancing a quality of image data used for treatment diagnosis of the doctor.

The effects of the present disclosure are not limited to the aforementioned effect, and other effects, which are not mentioned above, will be apparent to a person having ordinary skill in the art from the following disclosure.

BRIEF DESCRIPTION OF THE DRAWINGS

The above and other aspects, features and other advantages of the present disclosure will be more clearly understood from the following detailed description taken in conjunction with the accompanying drawings, in which.

DETAILED DESCRIPTION OF THE PREFERRED EMBODIMENT

The present disclosure may have various modifications and various exemplary embodiments and specific exemplary embodiments will be illustrated in the drawings and described in detail in the detailed description. However, this does not limit the present disclosure to specific exemplary embodiments, and it should be understood that the present disclosure covers all the modifications, equivalents and replacements included within the idea and technical scope of the present disclosure. In describing each drawing, like reference numerals refer to like elements.

Terms including as first, second, A, B, and the like are used for describing various constituent elements, but the constituent elements are not limited by the terms. The terms are used only to discriminate one constituent element from another component. For example, a first component may be referred to as a second component, and similarly, the second component may be referred to as the first component without departing from the scope of the present disclosure. A term 'and/or' includes a combination of a plurality of associated disclosed items or any item of the plurality of associated disclosed items.

It should be understood that, when it is described that a component is "connected to" or "accesses" another component, the component may be directly connected to or access the other component or a third component may be present therebetween. In contrast, it should be understood that, when it is described that an element is "directly connected to" or "directly access" another element, it is understood that no element is present between the element and another element.

Terms used in the present application are used only to describe specific exemplary embodiments, and are not intended to limit the present disclosure. A singular form may include a plural form if there is no clearly opposite meaning in the context. In the present application, it should be understood that term "include" or "have" indicates that a feature, a number, a step, an operation, a component, a part or the combination thereof described in the specification is present, but does not exclude a possibility of presence or addition of one or more other features, numbers, steps, operations, components, parts or combinations thereof, in advance.

If not contrarily defined, all terms used herein including technological or scientific terms have the same meanings as those generally understood by a person with ordinary skill in the art. Terms which are defined in a generally used dictionary should be interpreted to have the same meaning as the meaning in the context of the related art, and are not interpreted as an ideal meaning or excessively formal meanings unless clearly defined in the present application.

Hereinafter, exemplary embodiments of the present disclosure will be described in detail with reference to the accompanying drawings.

Figure 1:
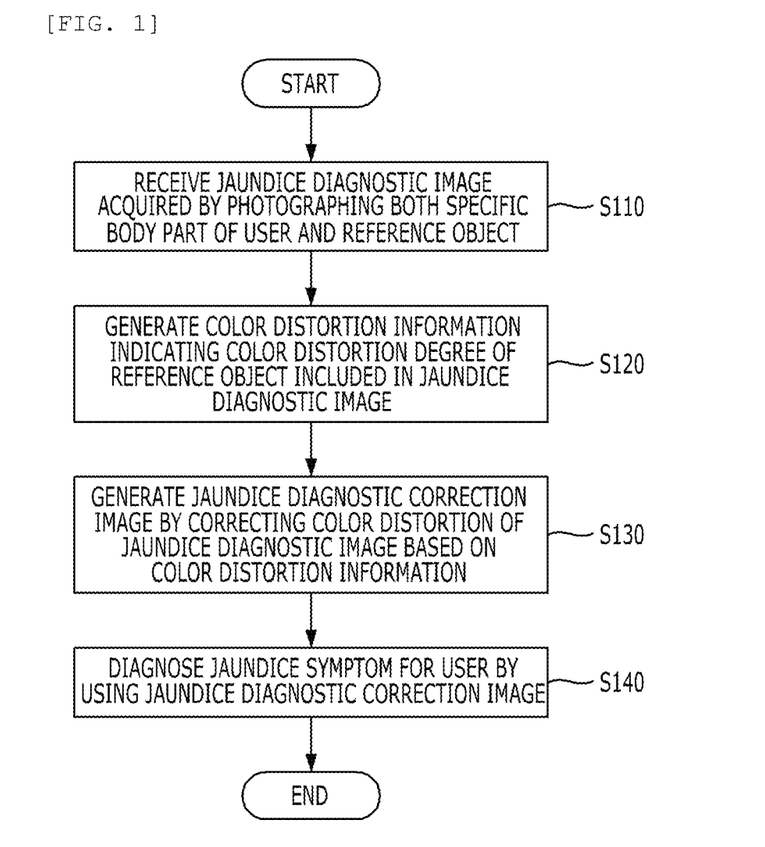
FIG. 1 is a flowchart for describing a method for jaundice diagnosis based on an image according to an exemplary embodiment of the present disclosure.

FIG. 1 is a flowchart for describing a method for jaundice diagnosis based on an image according to an exemplary embodiment of the present disclosure.

In step 110, a jaundice diagnosing apparatus receives a jaundice diagnostic image acquired by photographing both a specific body part of a user and a reference object.

In this case, the jaundice diagnostic image may be an image photographed at a place where the user is presently located and the specific body part of the user may be a face, an eyeball, or the like of the user or a body part such as a wrist or the like in which a skin of the user may be confirmed.

In addition, the reference object may be a white object such as a white paper, a white post-it, a white cloth, a white plastic model, a white hat, a white band, and a white eyeglass as an object which becomes a reference for correcting colors of a face skin and the eyeball of the user or a color band, a color table, a patch, or the like composed of a plurality of colors.

Further, the jaundice diagnostic image may be obtained by a method in which the user photographs the reference object by holding the reference object in a hand or by placing the reference object at a position near the body part of the user and obtained by a method in which the reference object is photographed while being worn or attached onto the specific body part of the user.

For example, the reference object may be composed of a single region having a white color or an eye patch composed of a plurality of regions each having a different color, which will be described later with reference to FIG. 2. Further, the reference object may be a patch composed of a plurality of regions having a white color and at least one different color, which will be described later with reference to FIGS. 4 and 5.

Meanwhile, the reason for creating the jaundice diagnostic image by photographing both the specific body part of the user and the reference object is that the color of the body part of the user may be distorted depending on an environment (especially, an illumination environment) of the place where the body part of the user is photographed.

For example, when a user with a jaundice symptom visits a medical office of a hospital, in a case where the eyeball of the user is photographed under a fluorescent lamp and thereafter, in a case where the eyeball of the user is photographed while the user turns on an incandescent lamp in his or her home, even if the color of the eyeball of the user is not actually changed, the eyeball of the user shows a more yellow color in the image photographed in the incandescent lamp. Therefore, there is a need to correct such color distortion, so that the jaundice diagnostic image acquired by photographing the reference object together is created.

In another exemplary embodiment, a user interface for photographing the jaundice diagnostic image provided by the jaundice diagnosing apparatus when the user photographs the jaundice diagnostic image may be used, which will be described later with reference to FIG. 3.

In step 120, the jaundice diagnosing apparatus generates color distortion information indicating a color distortion degree of the reference object included in the jaundice diagnostic image.

In this case, the color distortion information may be generated based on illuminance of the environment in which the jaundice diagnostic image is photographed, photographing related setting values (aperture value, shutter speed, ISO, etc.) of a user device that photographs the jaundice diagnostic image, a lens aberration for a lens mounted on the user device, and the like.

Here, the user device includes all devices having a photographing function to photograph the image of the user such as a smart phone, a mobile phone, a notebook computer, a desktop computer, and like of the user and a communication function to transmit the jaundice diagnostic image to the outside and the jaundice diagnosing apparatus may be the user device or a device mounted on the user device.

At this time, the color distortion information may be information based on a color temperature.

More specifically, the jaundice diagnosing apparatus may generate as the color distortion information color temperature difference information which is a difference value between a first color temperature which is a color temperature of the reference object in a reference image obtained by photographing a reference object (or the reference body and the specific body part of the user) under a previously stored reference light source and a second color temperature which is a color temperature of the reference object included in the jaundice diagnostic image.

Here, the reference light source may be a virtual light source based on a specific color temperature (5600 K or 3200 K) or may be an actual light source of a hospital medical office that the user visits previously.

For example, when the reference object is white A4 paper, since a first color temperature value which is the color temperature for the white A4 paper in the reference image in which the white A4 paper is photographed under the light source based on a specific color temperature is already known, the jaundice diagnosing apparatus generates the color temperature difference information which is the difference value between the first color temperature value and the second color temperature which is the color temperature of the reference object included in the jaundice diagnostic image to generate the color distortion information. In this case, the jaundice diagnosing apparatus may store only the first color temperature value for the white A4 paper in advance instead of storing only the reference image in advance.

In addition, in the case of the reference image generated by photographing the reference object in the medical office of the hospital or photographing both the reference object and the user when the user with the jaundice symptom visits the hospital, the reference light source becomes the light source installed in the medical office of the hospital and the color temperature of the reference object in the reference image becomes the first color temperature.

In another exemplary embodiment, the color distortion information may be information based on luminance Y.

For example, when the reference image is in YCbCr format and the jaundice diagnostic image is in RGB format, the jaundice diagnosing apparatus may convert the jaundice diagnostic image in the RGB format into the YCbCr format to generate a jaundice diagnostic conversion image and thereafter, calculate a first luminance distribution function which is a cumulative probability density function for the luminance values Y of all pixels belonging to the jaundice diagnostic conversion image and generate the calculated first luminance distribution function as the color distortion information.

In step 130, the jaundice diagnosing apparatus generates a jaundice diagnostic correction image by correcting the color distortion of the jaundice diagnostic image based on the color distortion information.

In this case, when the color distortion information is the color temperature difference information, the jaundice diagnosing apparatus generates the jaundice diagnostic correction image by correcting the color temperature of the jaundice diagnostic image so that the color temperature of a basic object of the jaundice diagnostic image becomes equal to the first color temperature based on the color temperature difference information.

When the color distortion information is a first luminance distribution function, the jaundice diagnosing apparatus calculates a second luminance distribution function, which is a cumulative probability density function for the luminance values Y of all the pixels belonging to the reference image in the YCbCr format and corrects the jaundice diagnostic image corresponding to the first luminance distribution function to have the second luminance distribution function to generate the jaundice diagnostic correction image.

This will be described below with reference to FIG. 10.

Figure 10:
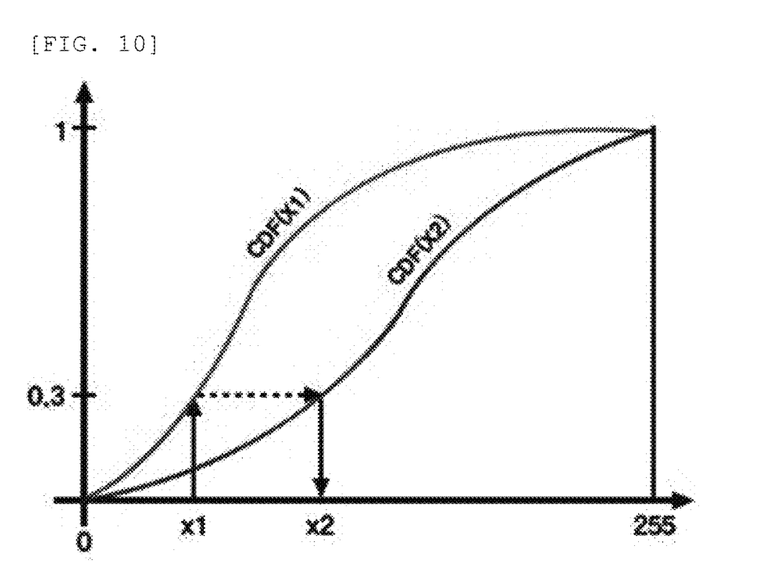
FIG. 10 is a diagram illustrating a method for creating a correction image for jaundice diagnosis using a luminance distribution function according to an exemplary embodiment of the present disclosure.

FIG. 10 is a diagram illustrating a method for creating a correction image for jaundice diagnosis using a luminance distribution function according to an exemplary embodiment of the present disclosure.

Referring to FIG. 10, a CDF(X1) graph represents the first luminance distribution function corresponding to the jaundice diagnostic image requiring correction, a CDF(X2) graph represents the second luminance distribution function corresponding to the reference image and a horizontal axis represents the luminance value and a vertical axis represents the cumulative probability density value.

In FIG. 10, a process of correcting the first luminance distribution function to match the second luminance distribution function is a process of converting the luminance value of the pixel in the first luminance distribution function (CDF(X1) graph) into the luminance value of the pixel in the second luminance distribution function (CDF(X2) graph) having the same cumulative probability density value.

For example, when the luminance value of pixel x1 in the first luminance distribution function (CDF(X1) graph) is to be corrected, pixel x2, which is the pixel having the cumulative probability density value equal to 0.3, which is the cumulative probability density value of the pixel x1 is found in the second luminance distribution function (CDF(X2) graph) and the luminance value of the pixel x1 is converted into the luminance value of the pixel x2.

In step 140, the jaundice diagnosing apparatus diagnoses the jaundice symptom for the user using the jaundice diagnostic correction image.

Preferably, when diagnosing the jaundice symptom for the user, the jaundice diagnosing apparatus transmits a jaundice diagnosis request including the jaundice diagnostic correction image and requesting the jaundice diagnosis for the user to a diagnosis server (e.g., a server provided in the hospital) and receives a jaundice diagnosis result which is a diagnosis result for the jaundice diagnosis request from the diagnosis server to perform diagnosis.

In another exemplary embodiment, the jaundice diagnosing apparatus may perform the jaundice diagnosis by directly analyzing the jaundice diagnostic correction image without transmitting the jaundice diagnostic correction image to the diagnosis server.

Meanwhile, the diagnosis server may determine the jaundice diagnosis result based on an image analysis result for the jaundice diagnostic correction image.

In yet another exemplary embodiment, the diagnosis server may determine the jaundice diagnosis result based not only on the image analysis result, but also on medical history information for the user, treatment information for the other person with the jaundice symptom, and the like.

In this case, the diagnosis server may estimate the disease of the user based on at least one of the medical history information for the user and the treatment information for the other person and generate the jaundice diagnosis result including health risk information indicating whether the jaundice symptom of the user is at risk for health based on a correlation between the estimated user's disease and the image analysis result. For example, the health risk of the jaundice symptom when the user is suffering from disease A may be higher than the health risk of the jaundice symptom when the user is suffering from disease B. Therefore, even a user suffering from the same degree of jaundice symptom may be judged to have a high health risk if the user is suffering from disease A and the health risk may be judged not to have the high health risk if the user is suffering from disease B.

In this case, the jaundice diagnosing apparatus may output a message asking the user who is suffering from disease A to visit the hospital as soon as the health risk is high.

On the other hand, the disease suffered by the user may be automatically estimated by machine learning based on the medical history information for the user, the medical treatment information for the other person, or the like, but may be determined by the doctor himself/herself.

In addition, the jaundice diagnosis result may be automatically determined through image analysis and various data analyses as described above, but it may be determined by the doctor by using image analysis and various data analysis results as auxiliary data. At this time, the doctor considers the medical history information for the user together to diagnose and prescribe the jaundice symptom, so that it is possible to provide patient-customized diagnosis and prescription.

Thus, according to the exemplary embodiment of FIG. 1, after the user does not want to go to the hospital in advance or only visits the hospital for the first time for photographing the reference object and the user's specific body part, the user may receive the diagnosis of the jaundice symptom remotely without visiting the hospital each time in order to receive the diagnosis of the jaundice symptom thereof.

According to the present disclosure, big data-based deep learning is used to enhance medical accessibility of patients and improve the quality of medical services provided by the hospitals and the doctors.

Figure 2:
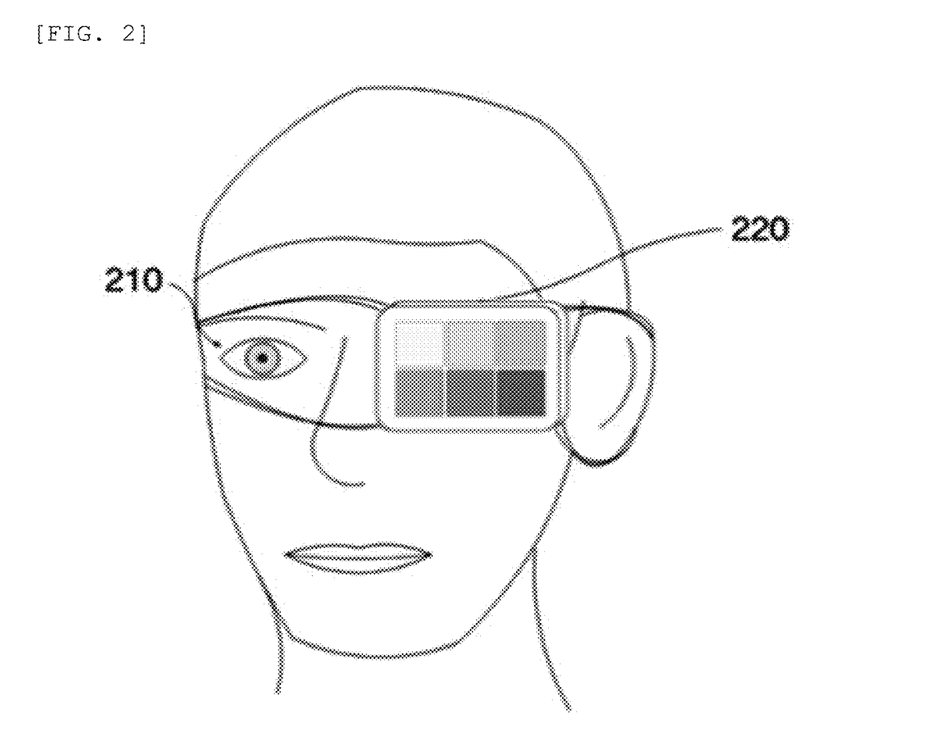
FIG. 2 is a diagram for describing a method for obtaining an image for jaundice diagnosis according to an exemplary embodiment of the present disclosure.

FIG. 2 is a diagram for describing a method for obtaining an image for jaundice diagnosis according to an exemplary embodiment of the present disclosure.

Referring to FIG. 2, illustrated is a scene in which the user wears an eye patch 220 constituted by a plurality of regions having different colors from his or her eyeball 210 and photographs the jaundice diagnostic image. In this case, the eye patch 220 may be constituted by the plurality of regions having different colors, but may be constituted by a single region having a white color.

In the case where the reference object is the eye patch 220 as described above, there is an advantage that the user may easily wear the eye patch 220 and photograph the image. Meanwhile, upon receiving the photographed jaundice diagnostic image as illustrated in FIG. 2, the jaundice diagnosing apparatus generates the jaundice diagnostic correction image by correcting the jaundice diagnostic image based on colors corresponding to the plurality of regions included in the eye patch 220.

For example, the jaundice diagnosing apparatus may generate the jaundice diagnostic correction image by calculating RGB pixel difference values by subtracting RGB pixel values for each of the colors under the reference light source from the RGB pixel values for each of the colors included in the jaundice diagnostic image and thereafter, adding the calculated the RGB pixel difference values to the RGB pixel values of respective pixels included in the jaundice diagnostic image.

Next, the jaundice diagnosing apparatus transmits the jaundice diagnostic correction image to the diagnosis server.

Subsequently, the diagnosis server extracts all or some of the pixels corresponding to the eyeball or facial skin of the user and selects jaundice pixels belonging to the RGB pixel value interval in which the extracted pixel values correspond to the jaundice.

Last, the jaundice diagnosing apparatus may diagnose whether the user has the jaundice symptom and a depth of the jaundice by comparing a ratio of jaundice pixels among the pixels extracted from the user's eyeball or facial skin with at least one threshold value.

For example, when the jaundice pixel ratio is 50% or more, there is the jaundice symptom and when the jaundice pixel ratio is 80% or more, it may be diagnosed that the jaundice is severe. The user of the jaundice diagnosing apparatus may change the threshold values as needed.

Figure 3:
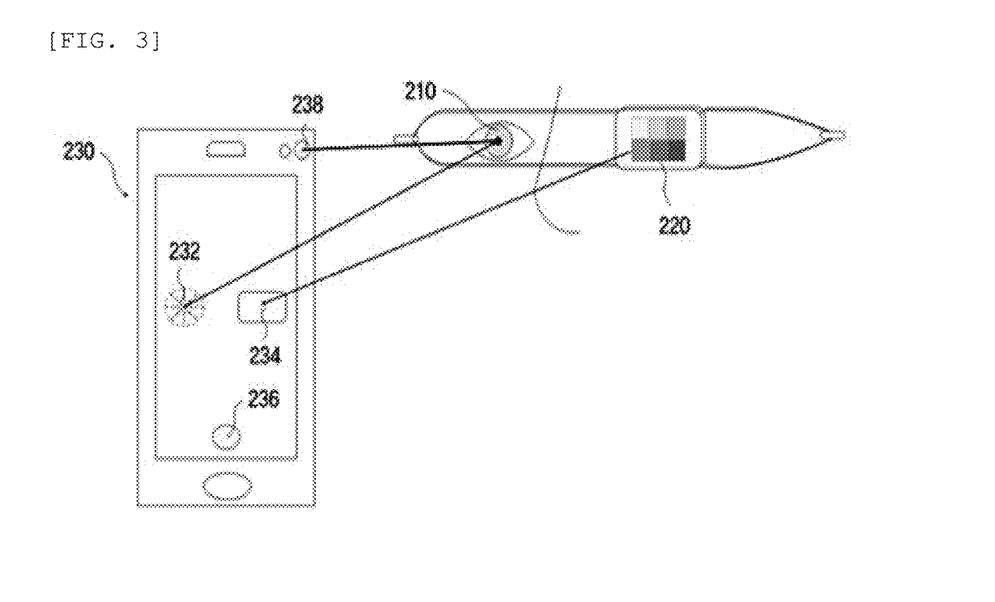
FIG. 3 is a diagram for describing a user interface according to an exemplary embodiment of the present disclosure.

FIG. 3 is a diagram for describing a user interface according to an exemplary embodiment of the present disclosure.

Referring to FIG. 3, user interfaces 232, 234, and 236 for photographing the jaundice diagnostic image are output to a user device 230 and the user aligns the eyeball 210 thereof with an eyeball region 232 represented by a circular shape on an upper left end of the user device 230, aligns the eye patch 220 of the user with an eye patch region 234 on an upper right end of the user device 230, and clicks on a photographing button 236 at a lower end to photograph the jaundice diagnostic image.

At this time, the user photographs the jaundice diagnostic image according to a photographing guideline provided by the user interfaces 232, 234, and 236 in real time.

For example, the user interfaces 232, 234, and 236 may display a message for notifying that the user slightly steps back when the user is too close to the user device and a message for notifying that the user strains his/her eyes when the eyeball 210 of the user is small and it is difficult to identify the eyeball.

Further, the photographing button 236 is used to adjust a focus of an object to be photographed or adjust sizes of an eyeball region 232 and an eye patch region 234 on the user interfaces 232, 234, and 236.

Figure 4:
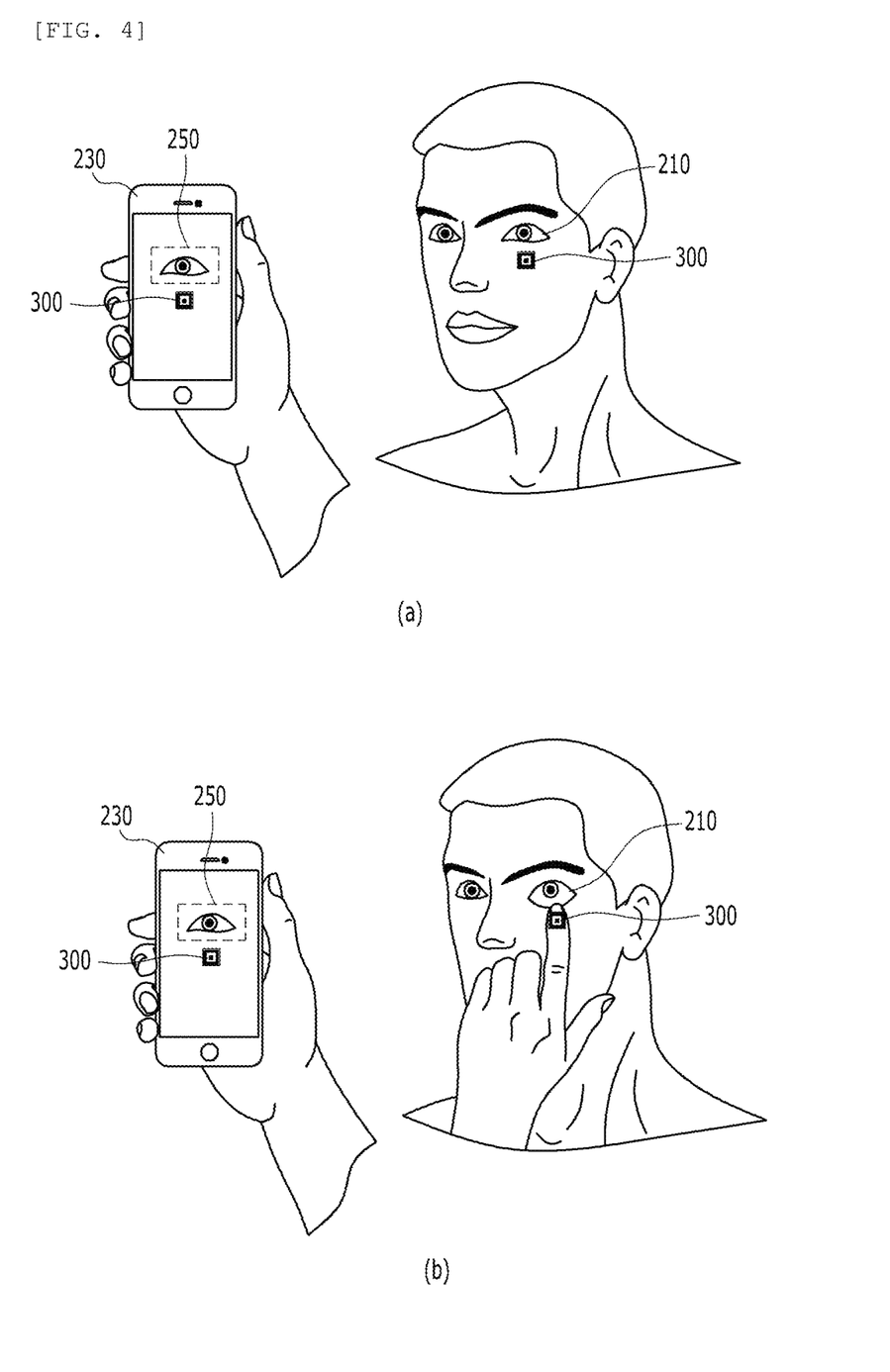
FIG. 4 is a diagram for describing a method for obtaining an image for jaundice diagnosis according to another exemplary embodiment of the present disclosure.
Figure 5:
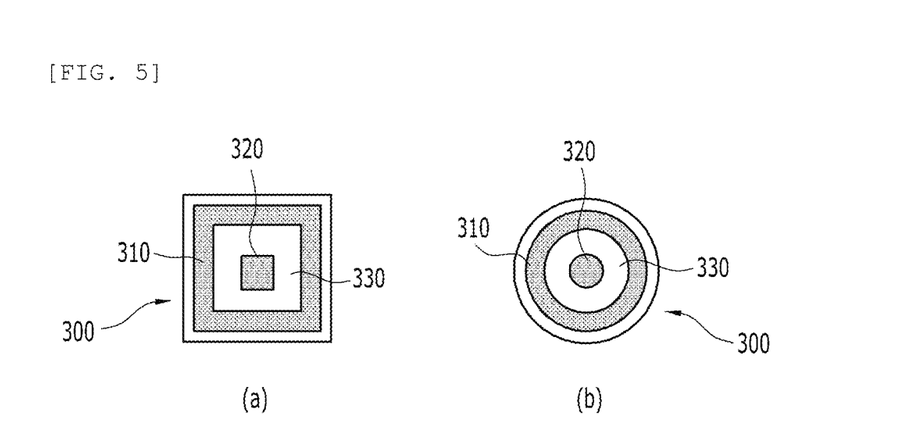
FIG. 5 is an exemplary view for describing a patch illustrated in FIG. 4.

FIG. 4 is a diagram for describing a method for obtaining an image for jaundice diagnosis according to another exemplary embodiment of the present disclosure and FIG. 5 is an exemplary diagram for describing a patch illustrated in FIG. 4.

FIG. 4A illustrates a scene in which the user attaches a patch 300 constituted by a color area having the white color and at least one different color onto his/her face and photographs the jaundice diagnostic image. Here, it is illustrated that the patch 300 is attached under the eyes, but the patch 300 may be attached to other body parts.

FIG. 4B illustrates a scene in which the patch 300 is attached onto a nail of a finger pulling a portion under the eye and the user photographs the jaundice diagnostic image when the user pulls the portion under the eye with the user's finger in order to make a sclera part of the eyeball more visible. Here, the fingers are used to widen the scope of the ocular sclera, but even any tool may be used as long as the tool may extend the scope of the ocular sclera in addition to the fingers and when the tool is used, the patch 300 may be attached within a predetermined distance from the eye. In this case, the tool may include the finger.

Meanwhile, the patch 300 to be attached for diagnosis of jaundice is used as an auxiliary tool for correcting the color distortion of the photographed image caused by a performance difference of different cameras and a surrounding environment and photographing an in-focus image and may be constituted by a plurality of regions having the white color and at least one different color and may be an attachment type. Accordingly, the patch 300 may have a structure in which the color regions having the white color and at least one different color are disposed on a front surface and an adhesive region for enabling detachment/attachment is formed on a back surface. A white region in the color regions disposed on the front surface is used as a reference for correcting the color of the jaundice diagnostic image and the remaining color regions may be used as a reference for acquiring the in-focus image. For example, the patch 300 may have a pattern in which a first region and a second region of the same color are cross-disposed with the white region interposed therebetween. In addition, the patch 300 should be detachable to the user's body (e.g., a face), a tool, and the like, and should be photographed together with the user's specific body part, and as a result, the patch 300 may have a predetermined size suitable for being attached to the user's body part (e.g., face), the tool, and the like. For example, the patch 300 may have a ten-coin size, pupil size, and the like. In addition, the patch may have various shapes including a square shape, a circular shape, an elliptical shape, and the like.

Referring to FIG. 5 for the patch 300, FIG. 5A illustrates a rectangular patch and FIG. 5B illustrates a circular patch. The patch 300 may be configured such that a white region 330 is disposed between a first black region 310 and a second black region 320. Here, the first and second black regions 310 and 320 may be used to obtain the in-focus image and the white region 330 may be used as a reference for correcting the color of the jaundice diagnostic image. In FIG. 5, the patch 300 is illustrated, in which the first black region 310 and the second black region 320 are cross-disposed with the white region 330 interposed therebetween to facilitate identification of the patch 300 and other body parts (e.g., eyeball), but the color regions of the patch 300 may be configured in various shapes.

Hereinafter, a method for jaundice diagnosis when the user attaches the patch 300 illustrated in FIG. 5 to the specific body part of the user will be described. When a photographing unit is driven for the jaundice diagnosis, the jaundice diagnosing apparatus 230 (or the user device) equipped with the photographing unit analyzes the image displayed through the photographing unit in real time before the image is photographed, detects the patch 300, determines an image when the patch 300 is detected as the in-focus image, and photographs the image. In this case, the photographed image may be the jaundice diagnostic image.

That is, the jaundice diagnosing apparatus 230 analyzes the image displayed through the photographing unit in real time before photographing the image and detects the edges of the first black region 310 and the second black region 320 by using an edge detection algorithm. At this time, as the edge detection algorithm, various algorithms may be used, which include a canny edge detector algorithm, a Roberts edge detection algorithm, a Sobel edge detection algorithm, a Prewitt edge detection algorithm, and the like.

When the edges of the first black region 310 and the second black region 320 are detected, the jaundice diagnosing apparatus determines that the image is in focus to automatically photograph the image at the corresponding point of time. Further, when the edges of the first black region 310 and the second black region 320 are detected, the jaundice diagnosing apparatus determines whether the detected image exists within a predetermined range of the image and when the detected edge exists within the predetermined range, the jaundice diagnosing apparatus 230 may determine that the image is in focus and automatically photograph the image at the corresponding point of time. Here, the predetermined range may be, for example, a range based on the center of the image.

At this time, the jaundice diagnosing apparatus 230 provides the photographing guideline through the user interface or voice so as to photograph the in-focus image. For example, the jaundice diagnosing apparatus 230 may output a message for notifying that the user slightly steps back when the user is too close to the user device and a message for notifying that the user strains his/her eyes when the eyeball 210 of the user is small and it is difficult to identify the eyeball. Further, when the edges of the first black region 310 and the second black region 320 are detected while a part of the first black region 310 is cut, the jaundice diagnosing apparatus 230 may output a message for moving in a direction in which the edges of the first black region 310 and the second black region 320 may be detected. Further, when the detected edges of the first black region 310 and the second black region 320 do not exist within a predetermined range of the image, the jaundice diagnosing apparatus 230 may output a message for moving the user to be positioned within a predetermined range.

In the case where the reference object is the patch 300, the user may easily attach the patch 300 and the jaundice diagnosing apparatus 230 (or the user device) automatically photographs the jaundice diagnostic image, and as a result, the user need not perform an operation of pressing the photographing button in order to photograph the jaundice diagnostic image.

When the jaundice diagnostic image is photographed, the jaundice diagnosing apparatus 230 generates the jaundice diagnostic correction image by correcting the jaundice diagnostic image based on the white color included in the patch 300 of the jaundice diagnostic image. That is, the jaundice diagnosing apparatus 230 may generate the jaundice diagnostic correction image by calculating pixel difference values by subtracting pixel values for the white color under the reference light source from the pixel value of the white region and thereafter, adding the calculated pixel difference value to the RGB pixel value of each of the pixels included in the jaundice diagnostic image.

The jaundice diagnosing apparatus 230 transmits the jaundice diagnostic correction image to the diagnosis server.

Then, the diagnosis server extracts all or some of the pixels corresponding to the eyeball or facial skin of the user and selects jaundice pixels in which the pixel values of the extracted pixels belong to the RGB pixel value interval corresponding to the jaundice. In this case, the diagnosis server searches a predetermined range based on a location of the patch to determine a location of an interest region for the jaundice diagnosis and extract the pixels of the interest region. Further, the interest region may be predetermined and the diagnosis server may extract the pixels of the predetermined interest region. For example, an eye region may be set as the interest region. Further, when the user directly selects the interest region in the jaundice diagnostic image, the diagnosis server may extract the pixel of the selected interest region.

Last, the jaundice diagnosing apparatus 230 may diagnose whether the user has the jaundice symptom and a depth of the jaundice by comparing a ratio of jaundiced pixels among the pixels extracted from the user's eyeball or facial skin with at least one threshold value.

An application for the jaundice diagnosis may be installed in the jaundice diagnosing apparatus 230 performing the above-described operation. Therefore, when the user executes the application for the jaundice diagnosis, a photographing mode is automatically driven and the jaundice diagnostic image is photographed only when the patch is detected, so that the user need not press the photographing button in order to photograph the image.

Figure 6:
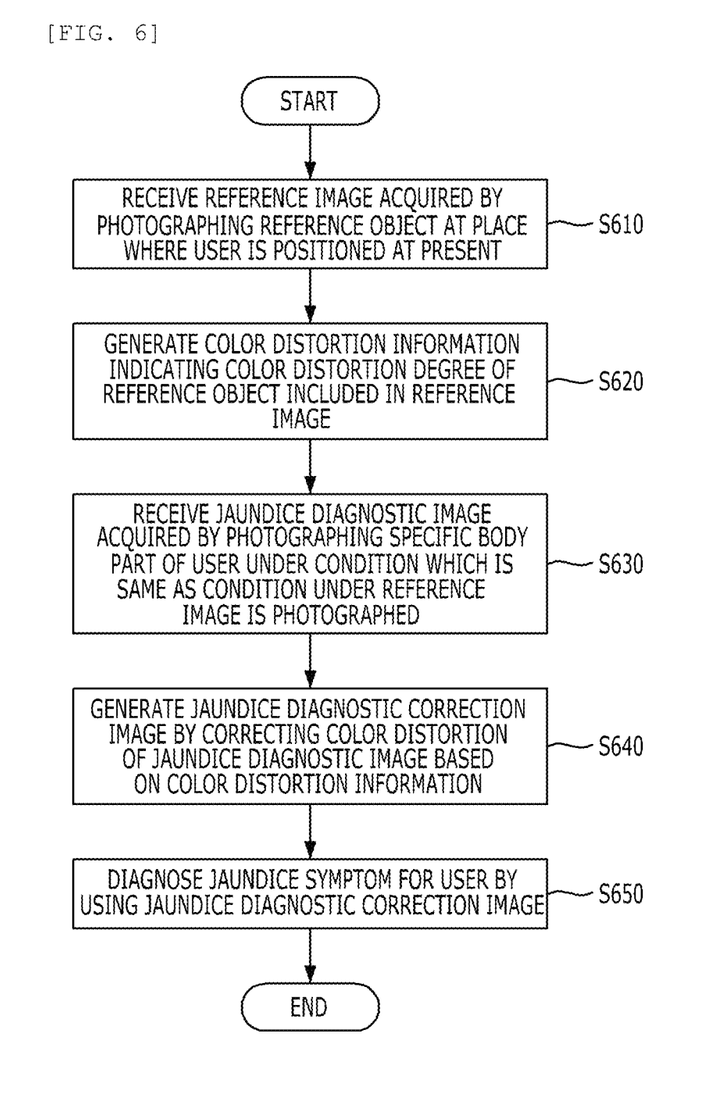
FIG. 6 is a flowchart for describing a method for jaundice diagnosis based on an image according to another exemplary embodiment of the present disclosure.

FIG. 6 is a flowchart for describing a method for jaundice diagnosis based on an image according to another exemplary embodiment of the present disclosure.

In step 610, a jaundice diagnosing apparatus receives a reference image acquired by photographing a reference object at a place where a user is positioned at present.

In step 620, the jaundice diagnosing apparatus generates color distortion information indicating a color distortion degree of the reference object included in the reference image.

The exemplary embodiment is different from the exemplary embodiment of FIG. 1 in that the color distortion information is generated by using the reference image acquired by photographing the reference object at the place where the user is positioned at present.

At this time, the color distortion information may be generated based on the color temperature difference information or may be generated using the luminance distribution function as described above.

In step 630, the jaundice diagnosing apparatus receives the jaundice diagnostic image acquired by photographing the specific body part of the user under a condition which is the same as a condition in which the reference image is photographed.

At this time, the same photographing condition means that the photographing is performed in the same light source, the same surrounding environment, and the same place.

In step 640, the jaundice diagnosing apparatus generates a jaundice diagnostic correction image by correcting the color distortion of the jaundice diagnostic image based on the color distortion information.

At this time, since the jaundice diagnostic image is photographed under the same condition as the reference image, it is possible to perform effective correction even if the color distortion of the jaundice diagnostic image is corrected using the color distortion information generated using the reference image.

In step 650, the jaundice diagnosing apparatus diagnoses the jaundice symptom for the user using the jaundice diagnostic correction image.

Figure 7:
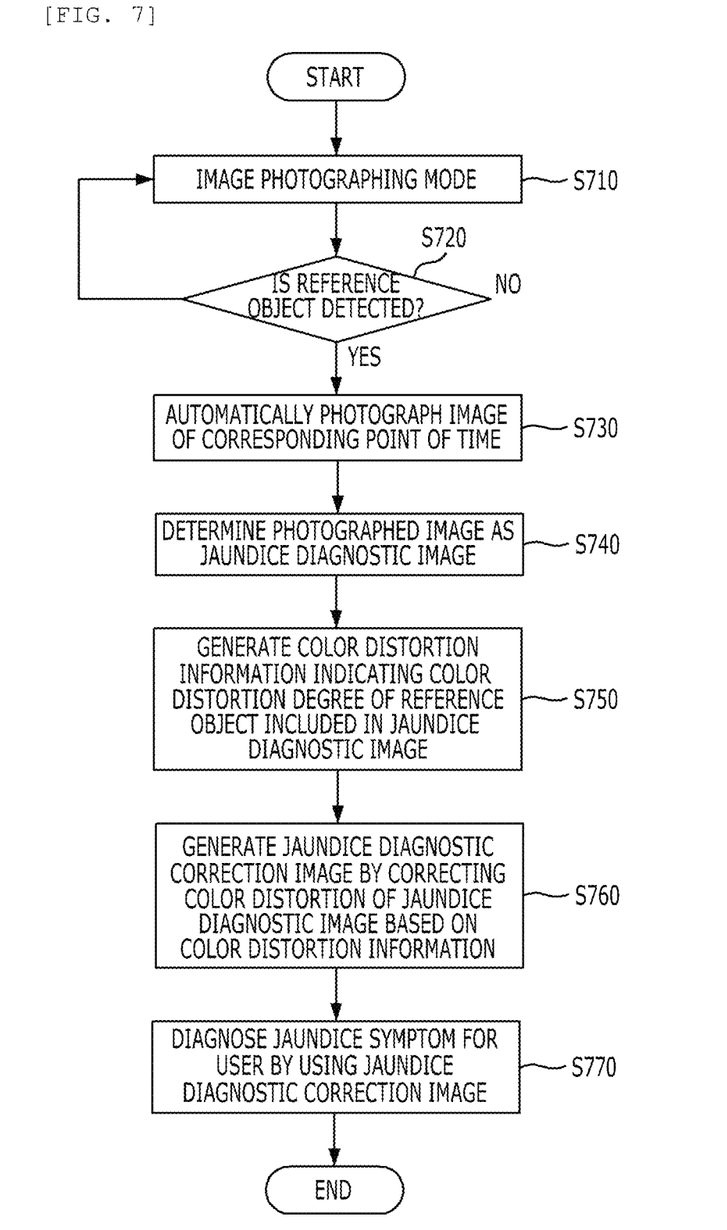
FIG. 7 is a flowchart for describing a method for jaundice diagnosis based on an image according to yet another exemplary embodiment of the present disclosure.

FIG. 7 is a flowchart for describing a method for jaundice diagnosis based on an image according to yet another exemplary embodiment of the present disclosure.

In step 710, when the image photographing mode of the photographing unit is driven, the jaundice diagnosing apparatus analyzes the image displayed through the photographing unit before the image photographing in step 720 to determine whether the reference object is detected.

That is, the jaundice diagnosing apparatus analyzes in real time the image displayed through the photographing unit before the image photographing to determine whether the edge of a predetermined patch is detected. For example, the jaundice diagnosing apparatus detects the edge of the remaining regions other than the white region among the color regions of the patch.

In step 730, when the edge of the reference object is detected, the jaundice diagnosing apparatus determines that the image at the point of time when the edge is detected is the in-focus image and automatically photographs the image at that point of time.

In step 740, the jaundice diagnosing apparatus determines the image photographed in step 730 as the jaundice diagnostic image. The jaundice diagnostic image may include the specific body part of the user and the reference object.

In step 750, the jaundice diagnosing apparatus generates color distortion information indicating a color distortion degree of the reference object included in the jaundice diagnostic image. At this time, the color distortion information may be generated based on the color temperature difference information or may be generated using the luminance distribution function as described above.

For example, when the reference object is an attachment type patch illustrated in FIG. 5, since a first color temperature value which is the color temperature for the white color of the patch in the reference image acquired by photographing the patch under the light source based on a specific color temperature is previously known, the jaundice diagnosing apparatus generates the color temperature difference information which is the difference value between the first color temperature value and the second color temperature which is the color temperature for the white color of the patch included in the jaundice diagnostic image to generate the color distortion information. In this case, the jaundice diagnosing apparatus may store only the first color temperature value for the white color instead of storing the reference image in advance.

In step 760, the jaundice diagnosing apparatus generates a jaundice diagnostic correction image by correcting the color distortion of the jaundice diagnostic image based on the color distortion information.

In step 770, the jaundice diagnosing apparatus diagnoses the jaundice symptom for the user using the jaundice diagnostic correction image.

Figure 8:
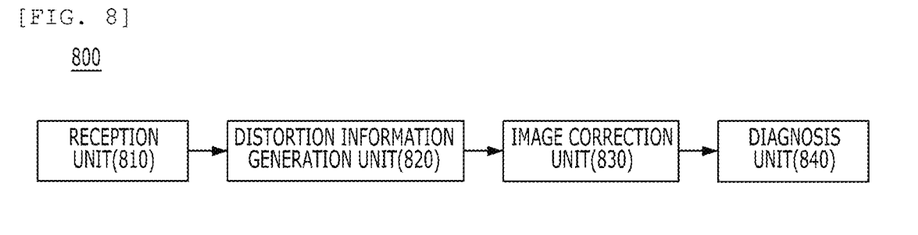
FIG. 8 is a flowchart for describing an apparatus for jaundice diagnosis based on an image according to an exemplary embodiment of the present disclosure.

FIG. 8 is a flowchart for describing an apparatus for jaundice diagnosis based on an image according to an exemplary embodiment of the present disclosure.

Referring to FIG. 8, a jaundice diagnosing apparatus 800 according to an exemplary embodiment of the present disclosure includes a reception unit 810, a distortion information generation unit 820, an image correction unit 830, and a diagnosis unit 840.

In step 810, the reception unit 810 receives the jaundice diagnostic image acquired by photographing both the specific body part of the user and the reference object at the place where the user is positioned at present.

The distortion information generation unit 820 generates color distortion information indicating a color distortion degree of the reference object included in the jaundice diagnostic image.

The image correction unit 830 generates a jaundice diagnostic correction image by correcting the color distortion of the jaundice diagnostic image based on the color distortion information.

The diagnosis unit 840 diagnoses the jaundice symptom for the user using the jaundice diagnostic correction image.

In this case, the diagnosis unit 840 may include a transmission unit (not illustrated) and a result processing unit (not illustrated).

The transmission unit transmits a jaundice diagnosis request including the jaundice diagnostic correction image and requesting the jaundice diagnosis for the user to the diagnosis server (not illustrated).

In another exemplary embodiment, instead of sending the jaundice diagnosis request to the diagnosis server, the transmission unit may transmit the jaundice diagnostic correction image directly to a device of the doctor.

At this time, the device of the doctor may include all devices having a communication function capable of receiving the jaundice diagnostic correction image and a display function capable of outputting the jaundice diagnostic correction image, such as a smart phone, a mobile phone, a notebook, a desktop computer, or the like of the doctor.

When the result processing unit receives a jaundice diagnosis result, which is the diagnosis result of the jaundice diagnosis request, from the diagnosis server (not illustrated) through the reception unit 810, the result processing unit performs the jaundice diagnosis for the user using the jaundice diagnosis result. Preferably, the jaundice diagnosing apparatus 800 according to an exemplary embodiment of the present disclosure may further include a user interface management unit (not illustrated) for outputting the user interface for photographing the jaundice diagnostic image.

The jaundice diagnosing apparatus 800 according to another embodiment of the present disclosure may operate as follows.

The reception unit 810 receives a reference image acquired by photographing a reference object at a place where a user is positioned at present.

The distortion information generation unit 820 generates color distortion information indicating a color distortion degree of the reference object included in the reference image.

The image correction unit 830 corrects the color distortion of the jaundice diagnosis image based on the color distortion information to generate the jaundice diagnostic correction image when the jaundice diagnostic image in which the user's specific body part is photographed is received under the same condition as the condition for photographing the reference image through the receiving unit 810.

The diagnosis unit 840 diagnoses the jaundice symptom for the user using the jaundice diagnostic correction image.

The jaundice diagnosing apparatus 800 according to yet another embodiment of the present disclosure may operate as follows.

The reception unit 810 receives a reference eyeball image obtained by photographing the user's eyeball in a first place where the photographing condition is known and receives the jaundice diagnostic image acquired by photographing the eyeball of the user at a second place other than the first place.

Here, the first place may be a hospital medical office and the second place may be a place other than the hospital medical office such as a home of the user.

The distortion information generation unit 820 compares an iris color in the reference eyeball image and the iris color in the jaundice diagnostic image to generate the color distortion information indicating the color distortion degree of the jaundice diagnostic image.

The reason why the iris color is compared to generate the color distortion information is that the iris color does not change even if the user has the jaundice symptom. Therefore, if the iris colors in the reference eyeball image and the jaundice diagnosis image are different, it may be regarded that the color distortion occurs and the degree of color distortion may also be known.

The image correction unit 830 generates a jaundice diagnostic correction image by correcting the color distortion of the jaundice diagnostic image based on the color distortion information.

The diagnosis unit 840 diagnoses the jaundice symptom for the user using the jaundice diagnostic correction image.

At this time, the diagnosis unit 840 can diagnose the jaundice symptom based on whether the color of the sclera of the user's eyeball included in the jaundice diagnosis correction image corresponds to the jaundice.

Figure 9:
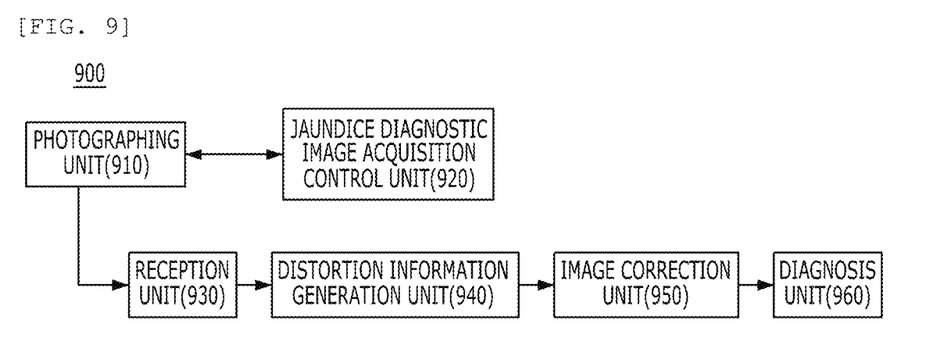
FIG. 9 is a flowchart for describing an apparatus for jaundice diagnosis based on an image according to another exemplary embodiment of the present disclosure.

FIG. 9 is a flowchart for describing an apparatus for jaundice diagnosis based on an image according to another exemplary embodiment of the present disclosure.

Referring to FIG. 9, a jaundice diagnosing apparatus 900 according to another exemplary embodiment of the present disclosure includes a photographing unit 910, a jaundice diagnostic image acquisition control unit 920, a reception unit 930, a distortion information generation unit 940, an image correction unit 950, and a diagnosis unit 960. However, not all illustrated components are required. The jaundice diagnosing apparatus 900 may be implemented by more components than the illustrated components and the jaundice diagnosing apparatus 900 may be implemented by fewer components.

The photographing unit 910 photographs the user's body-specific region and the reference object together. A predetermined photographing parameter may be set in the photographing unit 910. The predetermined photographing parameter may include, for example, an aperture value, whether a flash is emitted, a white balance condition, and the like.

Hereinafter, the present disclosure will be described by limiting the reference object to the patch for easy description.

When the application for the jaundice diagnosis is executed, the jaundice diagnostic image acquisition control unit 920 automatically drives the photographing unit 910 and analyzes the image displayed through the photographing unit 910 in real time before the image photographing to detect the patch, and automatically photographs the image at the time of detection of the patch. In this case, the photographed image may be the jaundice diagnostic image.

That is, the jaundice diagnostic image acquisition control unit 920 analyzes the image displayed through the photographing unit 910 in real time before image photographing and detects the edge of each color region of the patch using the edge detection algorithm. The jaundice diagnostic image acquisition control unit 920 determines that the image is in focus when the edge of the color region of the patch is detected and controls the photographing unit 910 to automatically photograph the image at that point of time. Further, when the edge for the color region of the patch is detected, the jaundice diagnostic image acquisition control unit 920 determines whether the detected image exists within a predetermined range of the image and when the detected edge exists within the predetermined range, the jaundice diagnostic image acquisition control unit 920 may determine that the image is in focus and automatically photograph the image at the corresponding point of time.

As described above, the jaundice diagnostic image acquisition control unit 920 controls to photograph the specific body part of the user and the patch while the image is in focus.

According to the exemplary embodiment, in order to photograph the jaundice diagnostic image, the jaundice diagnostic image may be photographed without a special operation of pressing the photographing button by the user.

The reception unit 930 receives the jaundice diagnostic image including the specific body part of the user and the patch photographed by the photographing unit 910.

The distortion information generation unit 940 generates color distortion information indicating a color distortion degree of the patch included in the jaundice diagnostic image. For example, the distortion information generation unit 940 compares the pixel value of the white color included in the patch with the pixel value of the reference color and generates the color distortion information based on a comparison result.

The image correction unit 950 generates a jaundice diagnostic correction image by correcting the color distortion of the jaundice diagnostic image based on the color distortion information.

The diagnosis unit 960 diagnoses the jaundice symptom for the user using the jaundice diagnostic correction image.

Meanwhile, the jaundice diagnosing apparatus 900 according to the present disclosure may further include a storage unit (not illustrated) storing an application for diagnosing jaundice. In addition, the storage unit stores the pixel value of the reference color which is the reference for generating the color distortion information by the distortion information generation unit 940.

In addition, the jaundice diagnosing apparatus 900 may further include a control unit (not illustrated) for controlling the operations of various components of the jaundice diagnosing apparatus 900. The control unit may store an application (or an applet) for allowing the user to diagnose the jaundice to be stored in the storage unit and control the jaundice to be diagnosed by driving the application.

In addition, the jaundice diagnosing apparatus 900 may further include a display unit (not illustrated) for controlling various information related with the operation of the jaundice diagnosing apparatus 900. In particular, the display unit may display various information including the image obtained through the photographing unit 910, a diagnosis result by the diagnosis unit, and the like. Such a display unit can be implemented through various display devices including an LCD, an LED, and the like.

In addition, the jaundice diagnosing apparatus 900 may further include an input unit (not illustrated) for receiving information from the user. Meanwhile, the input unit may be implemented as an input device such as a keypad, a touch panel, or the like and may be implemented as various input devices in addition to the input device. Further, the input unit may be implemented even in the form of a touch screen which is integrated with the display unit.

Figure 11:
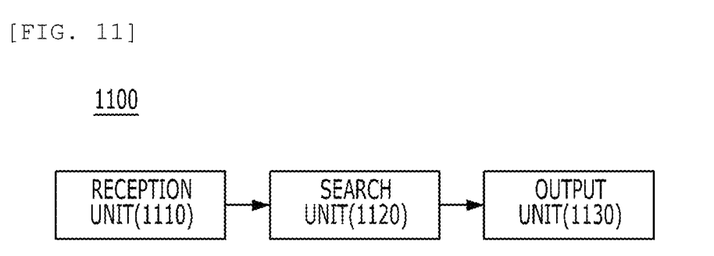
FIG. 11 is a flowchart for describing an assistant apparatus for jaundice diagnosis based on an image according to an exemplary embodiment of the present disclosure.

FIG. 11 is a flowchart for describing an assistant apparatus for jaundice diagnosis based on an image according to an exemplary embodiment of the present disclosure.

Referring to FIG. 11, a jaundice diagnosis assistant apparatus 1100 according to an exemplary embodiment of the present disclosure includes a reception unit 1110, a search unit 1120, and an output unit 1130.

In this case, the jaundice diagnosis assistant apparatus 1100 may be an apparatus mounted on the device of the doctor or the device of the doctor.

The reception unit 1110 receives the jaundice diagnostic correction image in which the color distortion is corrected as the image acquired by photographing both the specific body part of the user and the reference object.

In this case, the reception unit 1110 may receive the jaundice diagnostic correction image from the diagnosis server or the user device.

In another exemplary embodiment, the reception unit 1110 may receive the jaundice diagnosis request including the jaundice diagnostic correction image and requesting the jaundice diagnosis for the user.

The search unit 1120 may search the medical history information for the user from a patient medical history DB including medical history information for multiple jaundice patients.

In this case, the search unit 1120 may identify the user using identification information (e.g., a phone number of the smart phone) of the user device that transmits the jaundice diagnostic correction image and search the medical history information about the identified user.

In another exemplary embodiment, when the reception unit 1110 receives the jaundice diagnosis request, the jaundice diagnosis request may include user identification information for identifying the user and the search unit 1120 may search the medical history information for the user based on the user identification information included in the jaundice diagnosis request.

The output unit 1130 outputs the searched medical history information for the user and the jaundice diagnostic correction image.

According to the exemplary embodiment, since the doctor receives the medical history information for the user corresponding to the jaundice diagnostic correction image together with the jaundice diagnostic correction image without directly searching the medical history information for the user, convenience in medical examination is enhanced.

Preferably, an image-based jaundice diagnosis assistant apparatus 1100 according to an exemplary embodiment of the present disclosure may further include an analysis unit (not illustrated) that performs image analysis of the jaundice diagnostic correction image, thereby determining whether the user has the jaundice symptom and an image analysis result indicating the depth of jaundice. In this case, the output unit also outputs the image analysis result in addition to the medical history information for the user and the jaundice diagnostic correction image. In yet another exemplary embodiment, the analysis unit may further generate health risk information and in this case, the output unit outputs the health risk information to assist the jaundice diagnosis of the doctor.

The present disclosure has been described above with reference to preferred embodiments thereof. It is understood to those skilled in the art that the present disclosure may be implemented as a modified form without departing from an essential characteristic of the present disclosure. Therefore, the disclosed embodiments should be considered in an illustrative viewpoint rather than a restrictive viewpoint. The scope,of the present disclosure is defined by the appended claims rather than by the foregoing description, and all differences within the scope of equivalents thereof should be construed as being included in the present disclosure.

What is claimed is:

1. A method for diagnosing jaundice performed by a processor in a jaundice diagnosing apparatus based on an image, the method comprising:
   receiving, by the processor, a jaundice diagnostic image acquired by photographing both a specific body part of a user and a reference object;
   generating, by the processor, color distortion information indicating a color distortion degree of the reference object included in the jaundice diagnostic image;
   generating, by the processor, a jaundice diagnostic correction image by correcting color distortion of the jaundice diagnostic image based on the color distortion information; and
   diagnosing, by the processor, a jaundice symptom for the user by using the jaundice diagnostic correction image,
   wherein the reference object is an eye patch.

2. The method of claim 1, wherein the eye patch is constituted by a plurality of regions having a white color and at least one different color.

3. The method of claim 2, wherein in the eye patch, a pattern is formed, in which a first region and a second region of the same color are cross-disposed with a white region interposed therebetween.

4. The method of claim 1, wherein the eye patch is attached to a face within a certain distance from the eye of the user or attached to a tool or the face within a certain distance from the eye when the tool is used to widen the scope of the eye sclera.

5. The method of claim 1, further comprising:
   before the receiving of the jaundice diagnostic image,
   automatically photographing, by the processor, an image at a point of time when the reference object is detected by analyzing an image displayed through a camera provided in the jaundice diagnosing apparatus in real time,
   wherein the photographed image is a jaundice diagnostic image.

* * * * *